United States Patent
Yu et al.

(10) Patent No.: US 11,944,386 B2
(45) Date of Patent: Apr. 2, 2024

(54) INTELLIGENT ORTHOPEDIC EXTERNAL FIXING SYSTEM BASED ON CLOUD PLATFORM

(71) Applicant: AIKE (SHANGHAI) MEDICAL EQUIPMENT CO. LTD., Shanghai (CN)

(72) Inventors: Jian Yu, Shanghai (CN); Lai Zhang, Shanghai (CN); Junxiong Wang, Shanghai (CN); Hao Wang, Shanghai (CN); Renjing Qu, Shanghai (CN)

(73) Assignee: AIKE (SHANGHAI) MEDICAL EQUIPMENT CO. LTD., Shanghai (CN)

( * ) Notice: Subject to any disclaimer, the term of this patent is extended or adjusted under 35 U.S.C. 154(b) by 416 days.

(21) Appl. No.: 17/311,701

(22) PCT Filed: Jul. 8, 2020

(86) PCT No.: PCT/CN2020/100949
§ 371 (c)(1),
(2) Date: Jun. 8, 2021

(87) PCT Pub. No.: WO2020/259712
PCT Pub. Date: Dec. 30, 2020

(65) Prior Publication Data
US 2022/0022963 A1  Jan. 27, 2022

(30) Foreign Application Priority Data
Jun. 27, 2019 (CN) .......................... 201910565000.9

(51) Int. Cl.
*A61B 34/10* (2016.01)
*B33Y 50/02* (2015.01)
(Continued)

(52) U.S. Cl.
CPC .............. *A61B 34/10* (2016.02); *B33Y 50/02* (2014.12); *G06T 7/0012* (2013.01); *G06T 7/30* (2017.01);
(Continued)

(58) Field of Classification Search
CPC .............. A61B 34/10; A61B 2034/102; A61B 2034/105; A61B 2017/568; A61B 17/60;
(Continued)

(56) References Cited

U.S. PATENT DOCUMENTS

2004/0068187 A1    4/2004   Krause et al.
2020/0390503 A1*  12/2020   Casas .................... A61B 34/20
(Continued)

FOREIGN PATENT DOCUMENTS

CN    104905899 A    9/2015
CN    105662681 A    6/2016
(Continued)

OTHER PUBLICATIONS

International Search Report in PCT/CN2020/100949, issued by ISA, dated Sep. 25, 2020.
(Continued)

*Primary Examiner* — Bijan Mapar
(74) *Attorney, Agent, or Firm* — Zhu Lehnhoff LLP

(57) ABSTRACT

An intelligent orthopedic external fixing system based on a cloud platform, includes a cloud platform, an intelligent recognition unit and a Taylor spatial frame manufacturing module, wherein the intelligent recognition unit comprises an osteotrauma reconstruction module, a three-dimensional medical model registration module, a condition characteristic extraction module, an image recognition module, a personalized designed module and a basic module. According to the disclosure, the cloud platform integrates medical registration technology, computer image recognition tech-
(Continued)

nology, three-dimensional reconstruction technology and deep machine learning technology.

7 Claims, 2 Drawing Sheets

(51) Int. Cl.
    *G06T 7/00*         (2017.01)
    *G06T 7/30*         (2017.01)
    *G06T 17/00*       (2006.01)
    *G16H 30/40*      (2018.01)

(52) U.S. Cl.
    CPC ............. *G06T 17/00* (2013.01); *G16H 30/40* (2018.01); *A61B 2034/102* (2016.02); *A61B 2034/105* (2016.02); *G06T 2207/10081* (2013.01); *G06T 2207/20081* (2013.01); *G06T 2207/30008* (2013.01); *G06T 2210/41* (2013.01)

(58) Field of Classification Search
    CPC ....... B33Y 50/02; B33Y 50/00; G06T 7/0012; G06T 7/30; G06T 17/00; G06T 2207/10081; G06T 2207/20081; G06T 2207/30008; G06T 2210/41; G16H 30/40; G16H 20/40; G16H 50/20; G16H 50/50; G16H 20/30; Y02P 90/30; G06V 20/00; G06V 2201/03; B29C 64/386
    See application file for complete search history.

(56) References Cited

U.S. PATENT DOCUMENTS

2021/0166424 A1*   6/2021   Mullaney ................. G06T 7/74
2022/0265355 A1*   8/2022   Ferrante ................. A61B 34/30

FOREIGN PATENT DOCUMENTS

| CN | 106264690 A | 1/2017 |
|---|---|---|
| CN | 207965612 U | 10/2018 |
| CN | 110533763 A | 12/2019 |

OTHER PUBLICATIONS

Written Opinion of the International Search Report in PCT/CN2020/100949, issued by ISA, dated Sep. 25, 2020.

\* cited by examiner

INTELLIGENT ORTHOPEDIC EXTERNAL FIXING SYSTEM BASED ON CLOUD PLATFORM

TECHNICAL FIELD

The disclosure belongs to the field of medical instruments, and particularly relates to an intelligent orthopedic external fixing system based on a cloud platform.

BACKGROUND

Doctor Charles Taylor modified the ILizarov external fixing system to connect six telescopic extension rods obliquely to the proximal and distal end rings and they are freely rotatable at the point of connection. As long as the length of one of the extension rods is adjusted, one ring would change position relative to the other. A Taylor spatial frame is a standard six-degree-of-freedom parallel mechanism of Stewart platform, which has the characteristics of large stiffness, strong bearing capacity, non-cumulative position error, high stability, high precision and so on.

Since the interdisciplinary start of medical equipment, computer science and institutional science in China is relatively late, the Taylor external spatial frame, treatment system and treatment system in China are relatively slow to develop. Not only they are not widely used, but also key technologies, including treatment algorithm generation and parameter recognition methods, are mastered in foreign scientific and technological enterprises, so that doctors and patients in China bear high use cost when using such technologies, and in the production and use of advanced external spatial frames, such as Taylor spatial frames, the technical communication is inconvenient and the profit is extremely low for domestic medical treatment enterprises and doctors in the hospitals, which further hurts the power of development and the use range of domestic and foreign spatial frames, and the advanced orthopedic surgery treatment methods cannot provide benefit the Chinese people. Therefore, it is urgent to obtain the diagnosis and treatment system of advanced external spatial frames, such as Taylor spatial frames, with China's independent intellectual property rights through domestic independent research and development. An obstacle for limiting popularization of the Taylor external spatial frame is that recognition and acquisition of parameters such as malformation parameters, mounting parameters and the like in an existing orthopedic equipment and external spatial frame supporting diagnosis and treatment system at home and abroad need to be manually obtained by a doctor, the efficiency is not high, the accuracy is not good, and due to the fact that complex growth factors in a long-term rehabilitation process of a patient cannot be considered, residual malformations are easily generated after a treatment period is finished, and pain of the patient is increased.

SUMMARY OF THE DISCLOSURE

The disclosure aims to provide an intelligent orthopedic external fixing system based on a cloud platform, which integrates medical registration technology, computer image recognition technology, three-dimensional reconstruction technology and deep machine learning technology through the cloud platform, can automatically obtain malformation parameters, a design structure and mounting parameters, can personally customize orthopedic equipment, avoids dependence of traditional orthopedic treatment on doctors, reduces use difficulty of the Taylor spatial frame and improves treatment precision effect, from which patients gain benefits. In order to achieve the objects, the disclosure adopts the following technical solutions.

An intelligent orthopedic external fixing system based on a cloud platform, comprising a cloud platform, an intelligent recognition unit and a Taylor spatial frame manufacturing module,
  wherein the intelligent recognition unit comprises an osteotrauma reconstruction module, a three-dimensional medical model registration module, a condition characteristic extraction module, an image recognition module, a personalized designed module and a basic module;
  the osteotrauma reconstruction module transmits osteotrauma model information to the three-dimensional medical model registration module, the three-dimensional medical model registration module maps pixels of an osteotrauma model to a normal bone three-dimensional model, and the condition characteristic extraction module obtains malformation parameters on the mapped normal bone three-dimensional model; the image recognition module generates construction parameters, the basic module receives the construction parameters and signals from the personalized designed module and outputs a virtual manufacturing model to the cloud platform; the cloud platform outputs a manufacturing signal to a Taylor spatial frame manufacturing module; and the Taylor spatial frame manufacturing module generates a basic Taylor spatial frame unit.

Preferably, the intelligent orthopedic external fixing system based on a cloud platform further comprises a Taylor spatial frame unit based on the basic Taylor spatial frame unit, wherein the Taylor spatial frame unit comprises a proximal end ring, a distal end ring and an extension rod; the extension rod comprises a stud and a sleeve; a servo module is mounted inside the sleeve; the servo module receives signals from the cloud platform; an output end of the servo module is fixed with a lower end of the stud; the stud is slidably sleeved inside the sleeve; an upper end of the stud is hinged with the proximal end ring through a universal joint; and a lower end of the sleeve is hinged with the distal end ring through a universal joint.

Preferably, the intelligent orthopedic external fixing system based on a cloud platform further comprises an intelligent monitoring unit, an intelligent correction unit and a cloud database, wherein
  the intelligent monitoring unit generates healing process information; the intelligent monitoring unit is fixed on the sleeve;
  the cloud platform receives an output signal from the intelligent monitoring unit and outputs a signal to the cloud database; the intelligent correction unit receives an output signal from the cloud database and outputs a correction solution to the cloud database, and the cloud platform outputs the correction solution to the servo module.

Preferably, the intelligent monitoring unit comprises a plurality of sensors and a sensed information fusion module; and the sensed information fusion module fuses information of the sensors to generate the healing process information.

Preferably, the intelligent orthopedic external fixing system based on a cloud platform further comprises a client and a medical treatment end respectively connected with the cloud platform in signal connection.

Preferably, the intelligent orthopedic external fixing system based on a cloud platform further comprises a virtual unit, wherein the virtual unit receives the correction solution through the cloud platform and simulates and displays a bone healing process.

Preferably, the basic Taylor spatial frame unit comprises an upper end ring and an upper extension rod; and an upper end of the upper extension rod is hinged with the upper end ring, and a lower end of the upper extension rod is hinged with the proximal end ring.

Compared with the prior art, the disclosure has the advantages as follows.

1) The medical registration technology and the computer image recognition technology are adopted to reconstruct the three-dimensional model of a CT scanning result of the osteotrauma, the healthy bone model and the osteotrauma model are subjected to image registration through a machine learning method, the malformation parameters, the design structure and the mounting parameters are identified through graphic detection, the dependence of the traditional orthopedic treatment on doctors is avoided, the use difficulty of the Taylor spatial frame is reduced, and the treatment accuracy is improved.

2) The basic Taylor spatial frame unit is created by automatically reading the malformation parameters and taking a pre-stored basic model orthopedic equipment as a template according to the physiological condition and the treatment target of the patient output by the personalized designed module. The basic Taylor spatial frame unit meets the personalized requirements of patients, so that the treatment effect can be improved.

DETAILED DESCRIPTION OF THE PREFERRED EMBODIMENTS

The intelligent orthopedic external fixing system based on a cloud platform of the present disclosure will now be described in more detail with reference to the schematic diagrams, in which preferred embodiments of the present disclosure are shown. It shall be understood that those skilled in the art can modify the disclosure described herein while still achieving the advantageous effects of the present disclosure. Accordingly, the following description should be construed as broadly known to those skilled in the art and not as a limitation on the present disclosure.

Figure 1:
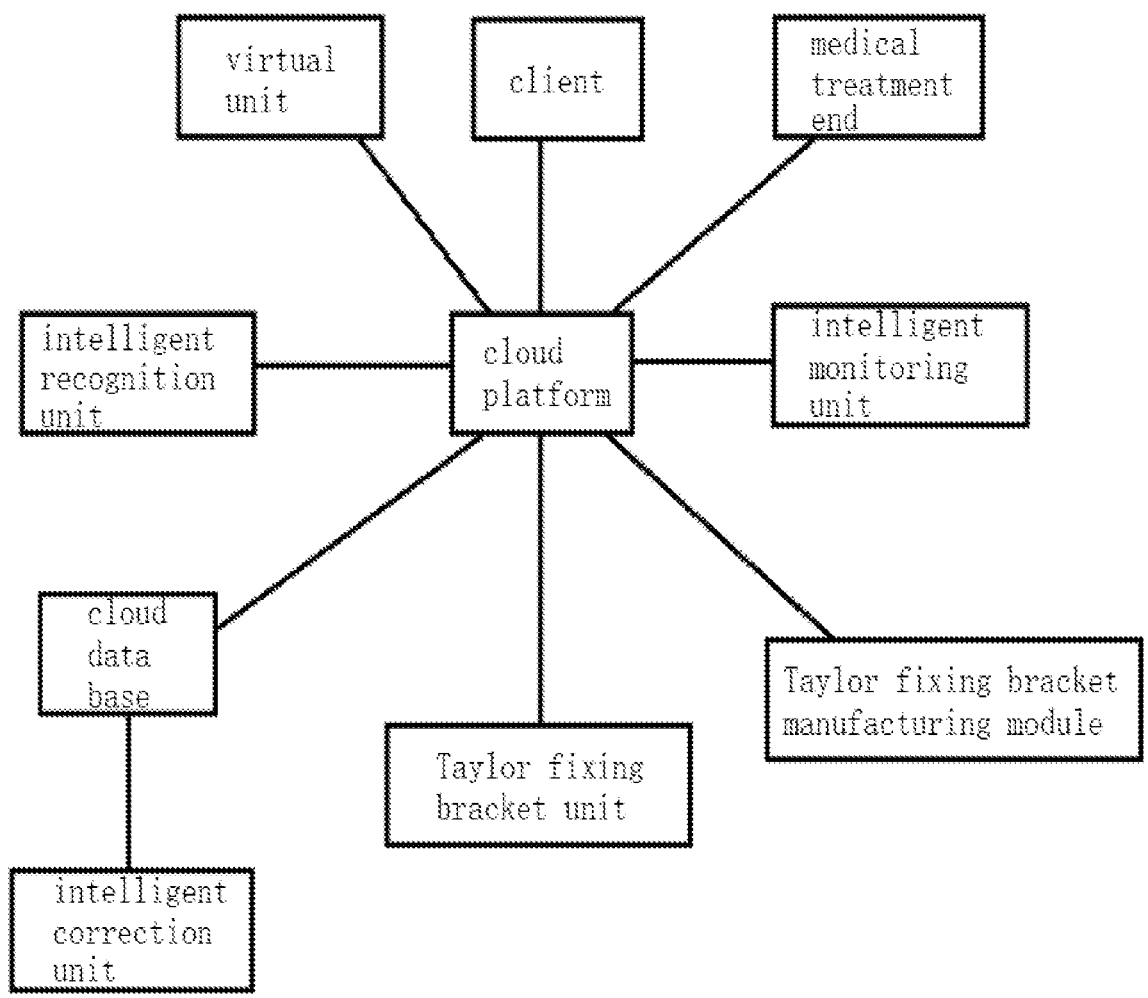
FIG. 1 is a structural block diagram of an intelligent orthopedic external fixing system based on a cloud platform according to an embodiment of the present disclosure.
Figure 2:
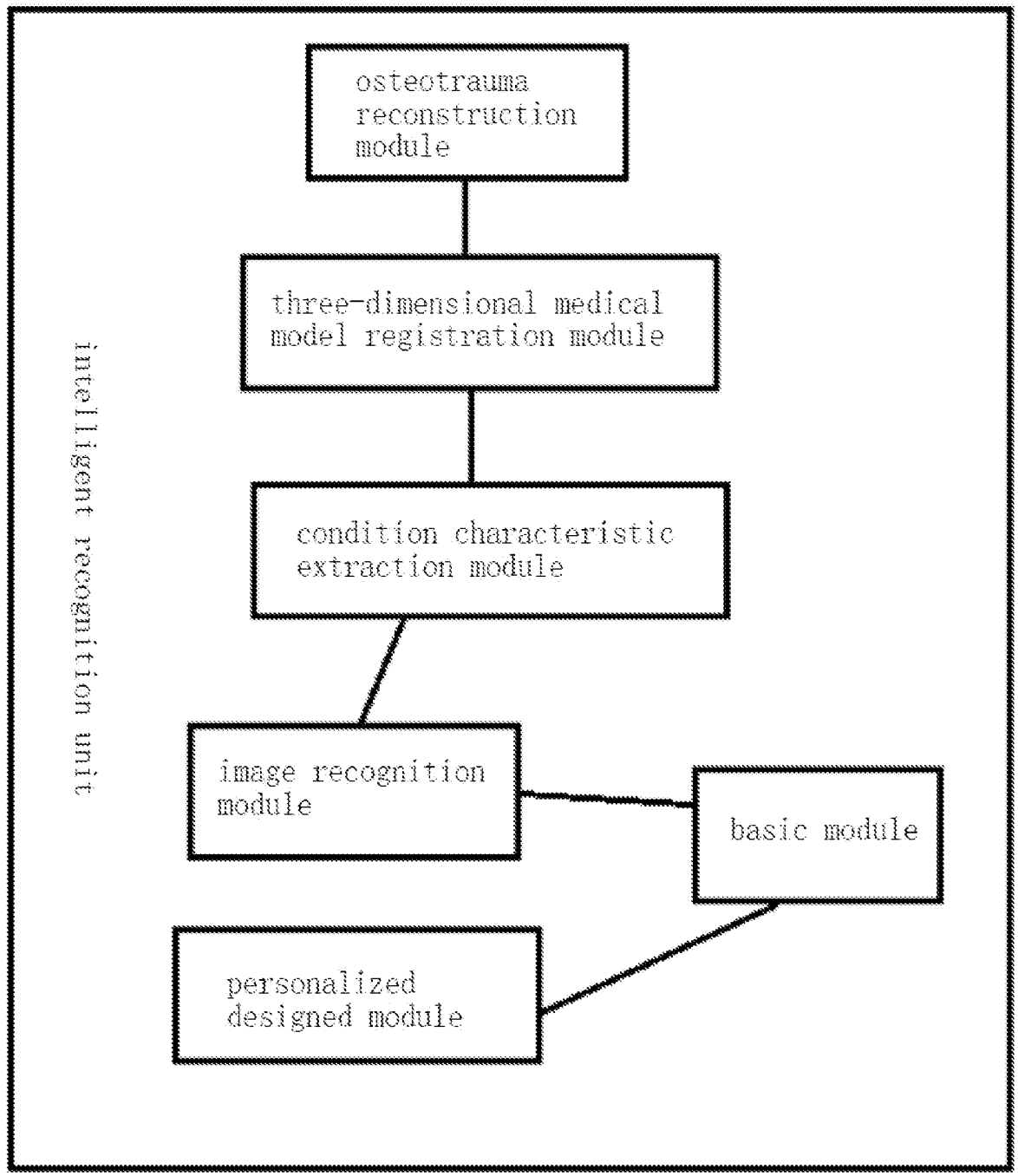
FIG. 2 is a structural block diagram of an intelligent recognition unit of FIG. 1.

FIG. 1 shows an intelligent orthopedic external fixing system based on a cloud platform, which comprises a cloud platform, an intelligent recognition unit and a Taylor spatial frame manufacturing module. As shown in FIG. 2, the intelligent recognition unit comprises an osteotrauma reconstruction module, a three-dimensional medical model registration module, a condition characteristic extraction module, an image recognition module, a personalized designed module and a basic module; the osteotrauma reconstruction module transmits osteotrauma model information to the three-dimensional medical model registration module, the three-dimensional medical model registration module maps pixels of an osteotrauma model to a normal bone three-dimensional model, and the condition characteristic extraction module obtains malformation parameters on the mapped normal bone three-dimensional model; the image recognition module generates construction parameters, the basic module receives the construction parameters and signals from the personalized designed module and outputs a virtual manufacturing model to the cloud platform; the cloud platform outputs a manufacturing signal to a Taylor spatial frame manufacturing module; and the Taylor spatial frame manufacturing module generates a basic Taylor spatial frame unit. The modules have the following signal connection relationship: the osteotrauma reconstruction module reconstructs the osteotrauma in a three-dimensional mode by utilizing functional and metabolic imaging technologies such as CT scanning and the like, and outputs the results in a point cloud mode after processing; the three-dimensional medical model registration module needs network training before registration. The network training process is as follows. The three-dimensional medical model registration is quickly and accurately carried out on the osteotrauma and the healthy bone three-dimensional model by using a machine learning method, and through the machine learning method, the alignment model and information for estimating some most alignment parameters can be obtained. After network training, the three-dimensional medical model registration module maps all pixels of the osteotrauma three-dimensional model into the normal bone three-dimensional model for reference simultaneously by using the parameters to realize registration. On the basis of three-dimensional model registration, the condition characteristic extraction module recognizes and detects the three-dimensional model based on deep learning, and marks and trains a feature point at a fractured bone to serve as a reference point. The condition characteristic extraction is automatically realized, set parameters are obtained, intervention sample training is carried out through auxiliary marks by doctors, parameter recognition results are optimized, and accurate malformation parameters are obtained. Therefore, the complex process of manually reading the malformation parameters by a doctor is avoided, the possibility of residual malformation caused by manual judgment errors is avoided, the dependence on the professional level of the doctor is avoided, and the use threshold of high-performance orthopedic equipment is lowered. The patient malformation condition, the body structure in the treatment area and the muscle and bone tissue structure can be obtained through image intelligent recognition detection, and the parameters are used as the construction parameters of the structure shape of the personalized orthopedic equipment. The existing orthopedic equipment is used as a basic template, and the construction parameters of the personalized orthopedic equipment are input to automatically generate the structure information of the orthopedic equipment which meets the individual treatment requirements of the patient and adapts to the individual physiological structure of the patient. A digital virtual manufacturing model for the orthopedic equipment is generated, which is uploaded to cloud platform to be evaluated and analyzed. The rationality and accuracy of the digital manufacturing model are judged through the treatment process simulation on the cloud platform, the manufacturing model is transmitted to an advanced precise manufacturing center (the Taylor spatial frame manufacturing module) such as 3D printing and the like through the cloud platform to carry out rapid machining molding after being accurate, and the orthopedic equipment with the strongest adaptability to individual patients and the most suitable treatment solution and no physiological repulsion is generated through personalized customization. Therefore, the function of personalized correction is realized.

In the embodiment, the intelligent orthopedic external fixing system based on a cloud platform further comprises a Taylor spatial frame unit based on the basic Taylor spatial frame unit, wherein the Taylor spatial frame unit, i.e., the orthopedic equipment described herein, comprises a proximal end ring, a distal end ring and an extension rod; the extension rod comprises a stud and a sleeve; a servo module is mounted inside the sleeve; in the present embodiment, the servo module is a step motor; the servo module receives signals from the cloud platform; an output end of the servo module is fixed with a lower end of the stud; a precise servo drive system (the servo module and the cloud platform) is used for controlling the movement of the orthopedic equipment, so that gaps are eliminated and the it is more stable in the running process of the threaded screw; the stud is slidably sleeved inside the sleeve; an upper end of the stud is hinged with the proximal end ring through a universal joint; and a lower end of the sleeve is hinged with the distal end ring through a universal joint. Further, the basic Taylor spatial frame unit comprises an upper end ring and an upper extension rod; and an upper end of the upper extension rod is hinged with the upper end ring, and a lower end of the upper extension rod is hinged with the proximal end ring. That is, the Taylor spatial frame unit is based on a Taylor space bone external spatial frame, but is provided in two layers. The first layer comprises an upper end ring, an upper extension rod and a proximal end ring; and the second layer comprises a proximal end ring, a distal end ring, and an extension rod. The two layers are respectively provided with steel needles and steel needle fixing seats.

In the embodiment, the intelligent orthopedic external fixing system based on a cloud platform further comprises an intelligent monitoring unit, an intelligent correction unit and a cloud database; and the intelligent monitoring unit generates healing process information. The intelligent monitoring unit is fixed on the sleeve; the cloud platform receives an output signal from the intelligent monitoring unit and outputs a signal to the cloud database; the intelligent correction unit receives an initial treatment solution and healing process information through the cloud database, adjusts the initial treatment solution in real time and outputs a final correction solution to the cloud database, and the cloud platform outputs the correction solution to the servo module. Since other tissue organs of the body, including nerves, blood vessels, muscles, skin, etc., are expected to be significantly elongated during correction, treatment solution optimization on the intelligent correction unit is required. In the process of network training, the intelligent correction unit obtains the path planning algorithm of the orthopedic equipment structure through researching and analyzing the kinematics and dynamics of different mechanical mechanisms of the orthopedic equipment, and generates the core of a correction solution; through the research of the correction treatment method, the related limitation requirements of tissue growth and stress are obtained, rooting is carried out through the data obtained by clinical correction treatment, quantitative relationship between the rooting and the treatment track is obtained, and an optimized correction path is generated by considering the possible influence of actual treatment and various aspects in daily life of patients on the treatment. After the network training is finished, the intelligent correction unit can output the safest treatment solution under the highest treatment efficiency. In this embodiment, the treatment solution is referred to as an electronic prescription.

In the embodiment, the intelligent monitoring unit comprises a plurality of sensors and a sensed information fusion module; and the sensed information fusion module fuses information of the sensors to generate the healing process information. Through the control of the precise sensor, the existing single-time human-based orthopedic equipment adjustment is converted into uninterrupted monitoring and adjustment based on the whole process, real-time feedback of the whole treatment process is guaranteed through real-time intelligent monitoring, and continuous adjustment and dynamic correction of the orthopedic equipment are realized.

In this embodiment, the intelligent orthopedic external fixing system based on a cloud platform further comprises a client and a medical treatment end respectively connected with the cloud platform in signal connection. The medical treatment end outputs the initial treatment solution to the cloud platform. The client outputs actual treatment condition. Treatment errors caused by accidental impact at the treatment accumulate to cause treatment failure or residual malformation, so that the treatment period is prolonged, the treatment pain is increased, the treatment effect is reduced, or irreversible damage is caused to a patient, and in order to avoid accidental interference in the treatment process, the treatment process of the patient needs to be monitored in the whole process, and doctors and patients can know the treatment progress in time and compare it with the correction solution, while the cloud platform is used for timely and accurately adjusting the correction solution.

In the embodiment, the intelligent orthopedic external fixing system based on a cloud platform further comprises a virtual unit, wherein the virtual unit receives the correction solution through the cloud platform and simulates and displays a bone healing process. Since the orthopedic process by the algorithm evaluation is irreversible, in the treatment solution obtained by the intelligent algorithm after obtaining the malformation parameters through characteristic extraction and the electronic prescription, there is possibility that errors are generated and the results are unreasonable or do not meet the actual treatment requirements of the actual treatment process, so simulation demonstration of the whole treatment process needs to be carried out before the treatment solution is executed, and the three-dimensional model reconstructed in the characteristic recognition is used for computer assisted graphic simulation. After a treatment solution obtained by an intelligent algorithm is executed by a patient, the treatment recovery process of the sick bone can be perfectly and vividly demonstrated, and in order to enable a doctor to obtain the immersive experience for the orthopedic treatment process and the change of the wounded part, the disclosure researches the whole process of simulating the bone healing of the patient by displaying the bone-orthopedic equipment of the patient in front of the doctor in a vivid three-dimensional image through a virtual reality technology. In the process, a doctor can observe the bone healing process from various angles by means of an immersion roaming function provided by the virtual reality, find a point that the generated solution does not accord with the actual situation according to one's own experience, adjust the treatment solution or the electronic prescription in time, and can know that the dangerous treatment period possibly occurring in the treatment process which can be avoided in advance to reduce risks, so that the treatment solution accords with the actual physical state of a patient. The feasibility and therapeutic effect of the present disclosure are ensured.

The working principle of the disclosure is as follows which comprises: uploading a three-dimensional CT cloud image or a multi-angle X-ray image of a target orthopedic position of a patient to a cloud platform, utilizing a machine learning and computer image recognition monitoring technology, intelligently recognizing malformation parameters through three-dimensional model reconstruction, generating a personalized orthopedic equipment by taking existing orthopedic equipment as a template according to individual treatment targets and physiological parameters of the patient, and generating the orthopedic equipment through an advanced molding and manufacturing technology; combining a multi-sensor data fusion technology, obtaining a treatment track and a treatment state in real time on the basis of a Taylor spatial frame unit and an intelligent correction unit, obtaining an accurate correction solution through optimization and correction in time, and meanwhile continuously controlling, by a control system composed of the servo module and the cloud platform, the orthopedic equipment under the guidance of the correction solution to perform dynamic correction.

In summary, in the intelligent orthopedic external fixing system based on a cloud platform provided by the embodiment of the disclosure, a personalized remote real-time refined medical system under the support of large data with digital measurement, intelligent recognition, expert-level diagnosis and overall process monitoring is constructed through a cloud technology.

The foregoing is only a preferred embodiment of the disclosure and is not intended to limit the disclosure in any way. Any person skilled in the art, without departing from the scope of the technical solution of the present disclosure, can make any form of equivalent substitution or modification on the technical solution and the technical content disclosed in the present disclosure, which still fall within the scope of protection of the present disclosure without departing from the content of technical solution of the present disclosure.

The invention claimed is:

1. An intelligent orthopedic external fixing system comprising a cloud platform and a Taylor spatial frame, wherein:
the system is configured to map pixels of an osteotrauma three-dimensional model to a normal bone three-dimensional model, to obtain malformation parameters on the mapped normal bone three-dimensional model, to generate construction parameters for the Taylor spatial frame, and to output a virtual manufacturing model to the cloud platform based on the construction parameters; the cloud platform is configured to output a manufacturing signal for manufacturing the Taylor spatial frame; and the system is configured to generate the Taylor spatial frame based on the manufacturing signal;
network training is performed before registration of a three-dimensional medical model and the network training comprises the following process: the three-dimensional medical model registration is carried out on the osteotrauma three-dimensional model and the normal bone three-dimensional model by using a machine learning method, and an alignment model and information for estimating alignment parameters is obtained through the machine learning method; after network training, the alignment parameters are used to achieve registration by mapping all pixels of the osteotrauma three-dimensional model into the normal bone three-dimensional model for reference simultaneously; based on three-dimensional model registration, the three-dimensional model is recognized and detected by utilizing deep learning, feature points at a fractured bone are marked and trained as reference points, condition characteristic extraction is automatically realized, set parameters are obtained, intervention sample training is carried out through doctor-assisted marks, parameter recognition results are optimized, and the malformation parameters are obtained;
the patient's malformation condition, the body structure in the treatment area, and the structure of the muscular and skeletal tissues are obtained through image intelligent recognition detection and are used as the construction parameters for the shape of the Taylor space frame; and
the virtual manufacturing model is based on information including the patient's malformation condition, the body structure in the treatment area, and the structure of the muscular and skeletal tissues.

2. The intelligent orthopedic external fixing system according to claim 1, wherein the Taylor spatial frame comprises a proximal end ring, a distal end ring and an extension rod; the extension rod comprises a stud and a sleeve; a servo module is mounted inside the sleeve; the servo module receives signals from the cloud platform; an output end of the servo module is fixed with a lower end of the stud; the stud is slidably disposed inside the sleeve; an upper end of the stud is hinged with the proximal end ring through a universal joint; and a lower end of the sleeve is hinged with the distal end ring through a universal joint.

3. The intelligent orthopedic external fixing system according to claim 2, further comprising a cloud database, wherein:
the system is configured to generate healing process information; and
the cloud platform receives an output signal comprising the healing process information and outputs a signal to the cloud database, the system is configured to receive an output signal from the cloud database and output a correction solution to the cloud database, and the cloud platform outputs the correction solution to the servo module.

4. The intelligent orthopedic external fixing system according to claim 3, further comprising a plurality of sensors, and the healing process information is generated by fusing information from the sensors.

5. The intelligent orthopedic external fixing system according to claim 3, further comprising a client and a medical treatment end respectively connected with the cloud platform in signal connection.

6. The intelligent orthopedic external fixing system according to claim 3, wherein the system is configured to receive the correction solution through the cloud platform and simulate and display a bone healing process.

7. The intelligent orthopedic external fixing system according to claim 3, wherein the Taylor spatial frame includes an upper end ring and an upper extension rod, an upper end of the upper extension rod is hinged with the upper end ring, and a lower end of the upper extension rod is hinged with the proximal end ring.

* * * * *